United States Patent

Shonaka et al.

[11] Patent Number: 5,843,734
[45] Date of Patent: Dec. 1, 1998

[54] ANTIFOAMING AGENT FOR FERMENTATION AND FERMENTATION PRODUCTION PROCESS USING THE SAME

[75] Inventors: Masafumi Shonaka; Keiko Hasebe; Masaharu Hayashi, all of Wakayama, Japan

[73] Assignee: Kao Corporation, Tokyo, Japan

[21] Appl. No.: 973,832

[22] PCT Filed: May 24, 1996

[86] PCT No.: PCT/JP96/01399

§ 371 Date: Dec. 8, 1997

§ 102(e) Date: Dec. 8, 1997

[87] PCT Pub. No.: WO97/00942

PCT Pub. Date: Jan. 9, 1997

[30] Foreign Application Priority Data

Jun. 23, 1995 [JP] Japan .................................. 7-157447

[51] Int. Cl.$^6$ ............................ C12N 1/00; B01D 19/04; C12P 13/04; C07C 51/43
[52] U.S. Cl. .......................... 435/106; 252/308; 252/309; 252/320; 252/321; 252/351; 252/358; 95/155; 435/41; 435/71.3; 435/183; 435/243; 435/812
[58] Field of Search ...................... 252/351, 358, 252/309, 320, 321, 308; 435/71.3, 106, 136, 812, 41, 183, 243; 554/168, 227; 95/155

[56] References Cited

U.S. PATENT DOCUMENTS 5,567,606  10/1996  Hayashi et al. .......................... 435/106

FOREIGN PATENT DOCUMENTS 6-54680  3/1994  Japan .

*Primary Examiner*—Herbert J. Lilling
*Attorney, Agent, or Firm*—Birch, Stewart, Kolasch & Birch, LLP

[57] ABSTRACT

An antifoaming agent for fermentation, which comprises (A) a reaction product obtained by the addition polymerization of 50 to 250 moles of ethylene oxide and propylene oxide (the molar ratio of ethylene oxide to propylene oxide= 1:1 to 1:4 ) to 1 mole of a mixture composed of an oil or fat and a polyhydric alcohol containing at least three hydroxyl groups; and (B) a fatty acid, an alcohol, a polyoxyalkylene polyhydric alcohol ether, a polyoxyalkylene alkyl ether, a polyoxyalkylene fatty acid ester, a polyoxyalkylene alkyl ether fatty acid ester and/or a polyoxyalkylene polymer. The above antifoaming agent has both foam-breaking effects and foam-inhibiting effects so that it has excellent antifoaming effects and does not adversely affect the fermentation production.

7 Claims, No Drawings us patent 5,843,734

ANTIFOAMING AGENT FOR FERMENTATION AND FERMENTATION PRODUCTION PROCESS USING THE SAME

This application claims the benefit under 35 U.S.C. §371 of prior PCT International Application No. PCT/EP96/02357 which has an International filing data of May 31, 1996, published as WO97/00942, Jan. 9, 1997, which designated the United States of America, the entire contents of which are hereby incorporated by reference.

FIELD OF THE INVENTION

This invention relates to an antifoaming agent for fermentation. More specifically, this invention relates to an antifoaming agent for fermentation, which has both foam-breaking effects and foam-inhibiting effects and is therefore excellent in defoaming effects, and does not adversely affect the fermentation production.

BACKGROUND OF THE INVENTION

In the conventional fermentation industry, for example, in the production of useful substances by deep-aerobic culture, a large amount of foams is formed, which causes various problems. Described specifically, a fermenter is filled with foams, which lowers a culturing capacity per unit volume and causes the culture solution to overflow from the fermenter. There is accordingly a demand for overcoming such a problem.

To suppress the formation of such foams, it is the common practice to add an antifoaming agent to a medium. As such an antifoaming agent, polyoxyalkylene polyhydric alcohol ethers, polyoxyalkylene alkyl ethers, polyoxyalkylene fatty acid esters, polyoxyalkylene alkyl ether fatty acid esters and the like are known (Japanese Patent Laid-Open Nos. 4282/1975, 121482/1975, 135298/1979, 169583/1981 and 35073/1990). In addition, antifoaming agents which break foams as soon as they are formed and thus immediately exhibit defoaming effects are also known (Japanese Patent Laid-Open No. 54680/1994).

These conventional antifoaming agents for fermentation, however, have not both the foam-breaking effects for breaking foams and foam-inhibiting effects for inhibiting the formation of foams from a liquid surface so that their defoaming effects are not sufficient. The use of an antifoaming agent having excellent foam-breaking effects and that having excellent foam-inhibiting effects in combination, on the other hand, offset their effects each other, leading to a problem that neither effect can be obtained. In addition, these antifoaming agents are accompanied with the problem that they inhibit the growth of microorganisms and production of target products, thus exerting a bad influence on the fermentation production.

An object of the present invention is therefore to provide an antifoaming agent for fermentation, which has both foam-breaking effects and foam-inhibiting effects and therefore has excellent defoaming effects, and does not adversely affect the fermentation production.

DISCLOSURE OF THE INVENTION

In view of the foregoing circumstances, the present inventors have conducted an extensive investigation. As a result, it has been found that an antifoaming agent for fermentation which is excellent in both foam-breaking effects and foam-inhibiting effects and does not adversely affect the fermentation production can be obtained by the use of a reaction product, which has been obtained by adding a predetermined amount of ethylene oxide and propylene oxide to a mixture of an oil or fat and a polyhydric alcohol, and a specific compound in combination, leading to the completion of the invention.

In one aspect of this invention, there is thus provided an antifoaming agent for fermentation, which comprises the following components (A) and (B):

(A) a reaction product obtained by the addition polymerization of 50 to 250 moles in total of ethylene oxide and propylene oxide (the molar ratio of ethylene oxide to propylene oxide=1:1 to 1:4) to 1 mole of a mixture composed of an oil or fat and a polyhydric alcohol containing at least three hydroxyl groups; and (B) at least one compound selected from the group consisting of:
(1) fatty acids,
(2) alcohols,
(3) polyoxyalkylene polyhydric alcohol ethers,
(4) polyoxyalkylene alkyl ethers,
(5) polyoxyalkylene fatty acid esters,
(6) polyoxyalkylene alkyl ether fatty acid esters, and
(7) polyoxyalkylene polymers.

In another aspect of this invention, there is also provided a process for the fermentation production of an amino acid, a carboxylic acid, an enzyme or an antibiotic, which comprises adding an antifoaming agent for fermentation, said agent containing the above components (A) and (B), to a culture medium in an amount of 0.0001 to 2 wt. % and culturing a microorganism in the resulting culture medium.

BEST MODES FOR CARRYING OUT THE INVENTION

A description will next be made of the component (A).

Examples of the oil or fat for use in the preparation of the reaction product, that is, the component (A) include vegetable oils such as coconut oil, palm oil, olive oil, soybean oil, rapeseed oil, linseed oil and castor oil, animal oils such as lard, tallow and bone oil, and fish oils; and hardened and semi-hardened oils thereof; and recovered oils available in the purification step of the above-exemplified oils.

Any polyhydric alcohol containing at least three hydroxyl groups can be used insofar as it is generally known. Preferred examples of it include polyhydric $C_{3-15}$ alcohols having three to six hydroxyl groups such as glycerin, sorbitol, glucose, trimethylolpropane, trimethylolethane, 1,2,4-butanetriol, 1,2,6-hexanetriol, 1,1,1-trimethylolhexane, pentaerythritol, erythrose, tetramethylol, cyclohexatriol, diglycerin and polyglycerin, with glycerin being particular preferred.

It is preferred to mix the oil or fat with the polyhydric alcohol at a molar ratio of 1:0.05 to 1:6, with 1:0.2 to 1:1 being particularly preferred.

The preferred molar ratio of ethylene oxide to propylene oxide, said ethylene oxide and propylene oxide being added to the above-described mixture of the oil or fat with the polyhydric alcohol, falls within a range of from 1:1 to 1:4, with a range of from 1:1.5 to 1:2.5 being particularly preferred. Ethylene oxide and propylene oxide are added in a total amount of 50 to 250 moles relative to one mole in total of the oil or fat and the polyhydric alcohol, with a total amount of 80 to 200 moles being particularly preferred.

There is no particular limitation imposed on the conditions of the addition reaction of ethylene oxide and propylene oxide. The addition reaction can be conducted under the conditions generally employed for the addition reaction of an alkylene oxide to an active-hydrogen-containing compound. Described specifically, to a mixture of the oil or fat and the polyhydric alcohol which has been prepared at the above molar ratio, a catalytic amount of an alkaline substance is added. Then, the resulting mixture is reacted with ethylene oxide and propylene oxide at about 100°–200° C. and 1–3 kg/cm² for several hours, whereby the addition reaction is conducted. At this time, ethylene oxide and propylene oxide can be added after mixing them (random addition) or added successively (block addition).

A description will next be made of the component (B).

Example of the fatty acid, that is, the component B(l) include linear or branched, saturated or unsaturated $C_{2-23}$ fatty acids, with $C_{10-18}$ ones being particularly preferred.

Examples of the alcohol, that is, the component B(2) includes linear or branched, saturated or unsaturated $C_{1-22}$ aliphatic alcohols, with linear saturated $C_{12-20}$ aliphatic alcohols being particularly preferred.

As the polyoxyalkylene polyhydric alcohol ether, that is, the component B(3), those containing at least oxypropylene or oxybutylene are preferred. Specific examples include those represented by the following formula:

wherein $R^1$ represents a residual group obtained by eliminating a hydrogen atom from all the hydroxyl groups of an aliphatic polyhydric alcohol or saccharide containing 2–8 hydroxyl groups; $x_1$ groups of AO each represents an oxyalkylene group selected from oxyethylene, oxypropylene and oxybutylene and at least one of the groups is oxypropylene or oxybutylene; AO can be added either by random addition or block addition; and $x_1$ stands for 1–250 and y stands for the number of oxygen atoms derived from the hydroxyl groups of $R^1$. Out of these, preferred are compounds each of which is represented by the following formula:

wherein $R^1$ and y have the same meanings as described above, one of $A^1$ and $A^2$ represents an ethylene group and the other one represents $C_{2-4}$ alkylene group, $l_1$ stands for 0–20, ml stands for 3–40 and $n_1$ stands for 3–30; and contains an oxyethylene group at a ratio of 5–30 wt. % of the total molecular weight. A block polymer having a [glycerin]-[(poly)oxypropylene]-[(poly)oxyethylene]-[(poly) oxypropylene] chain is particularly preferred.

As the polyoxyalkylene alkyl ether, that is, the component B(4), those containing at least oxypropylene or oxybutylene are preferred. Specific examples include those represented by the following formula:

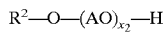

wherein AO has the same meaning as described above, $R^2$ represents a linear or branched $C_{1-24}$ alkyl or alkenyl group; $x_2$ stands for 1–200; and AO can be added either by random addition or block addition. Out of these, preferred are compounds each represented by the following formula:

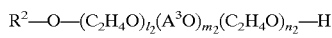

wherein $R^2$ has the same meaning as described above; $A^3$ represents a propylene or butylene group; $l_2$ stands for 1–10, $m_2$ stands for 10–80 and $n_2$ stands for 0–20. A block polymer having a [stearyl alcohol]-[(poly)oxy-ethylene]-[(poly) oxypropylene]-[(poly)oxyethylene] chain is particularly preferred.

As the polyoxyalkylene fatty acid ester, that is, the component B(5), those containing at least oxypropylene or oxybutylene are preferred. Specific examples include compounds each represented by the following formula:

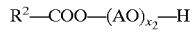

wherein $R^2$, AO and $x_2$ have the same meanings as described above. Out of these, compounds each represented by the following formula:

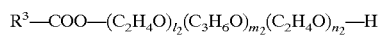

wherein $l_2$, $m_2$ and $n_2$ have the same meanings as described above and $R^3$ represents a linear or branched $C_{1-24}$ alkyl or alkenyl group, with compounds having an [oleic acid]-[(poly)oxyethylene]-[(poly)oxypropylene] chain being particularly preferred.

Examples of the polyoxyalkylene alkyl ether fatty acid esters, that is, the component B(6) include esters of the above-exemplified polyoxyalkylene alkyl ether and a saturated or unsaturated $C_{2-21}$ fatty acid.

As the polyoxyalkylene polymer, that is, the component B(7), those containing at least oxypropylene or oxybutylene are preferred. They may be block polymers or random polymers. Out of these, polypropylene glycol and polyoxyethylene-polyoxypropylene copolymer are more preferred, with those having an average molecular weight of 2,000 to 10,000 being particularly preferred. Specific examples include compounds each represented by the following formula:

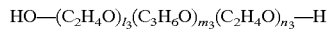

wherein $l_3$ and $n_3$ each stands for 0–20 and $m_3$ stands for 10–80. Out of these, compounds in which $l_3$ and $n_3$ each stands for 0 and $m_3$ stands for 10–80 are preferred, with those in which $l_3$ and $n_3$ each stands for 0 and $m_3$ stands for 40 to 70 being particularly preferred.

Out of these components (B), the component B(7) is more preferred.

These components (B) can be used either singly or in combination. Preferred examples of the combination include the combination of a fatty acid and a polyoxyalkylene polyhydric alcohol ether. In this case, they are mixed preferably at a weight ratio of 10:90 to 90:10.

The antifoaming agent according to the present invention for fermentation can be obtained by mixing the components (A) and (B) at a weight ratio of 5:95 to 95:5, preferably 20:80 to 70:30.

In addition to the components (A) and (B), various surfactants which are generally used for the fermentation production can be incorporated in the antifoaming agent of the present invention within the range of not inhibiting the fermentation production.

Examples of such surfactants include nonionic surfactants such as polyoxyethylene alkyl ethers, polyoxyethylene alkyl allyl ethers, sorbitan fatty acid esters, glycerin fatty acid esters, polyoxyethylene sorbitan fatty acid esters, polyoxyethylene sorbitol fatty acid esters, polyoxyethylene alkylamines and alkyl alkanol amides; anionic surfactants such as fatty acid salts, alkylsulfates, alkylbenzenesulfonates, alkylnaphthalenesulfonates, alkylsulfosuccinates, alkyldiphenylether disulfonates, alkylphosphates and polyoxyethylene alkylsulfates; and cationic surfactants such as alkyl amine salts, quaternary ammonium salts, alkyl betaines and amine oxides.

The antifoaming agent of the present invention for fermentation can be used by adding the components (A) and (B) in an amount of 0.0001 to 2 wt. %, particularly 0.001 to 1 wt. %, in total to a medium prior to the beginning of the culture of microorganisms or during the culture.

The antifoaming agent of the present invention for fermentation can be applied to the fermentation production of various substances. It can be employed suitably for the fermentation production of, for example, an amino acid, a carboxylic acid, an enzyme, an antibiotic or the like. Examples of the amino acid available by the fermentation production include glutamic acid, aspartic acid, citrulline, histidine, glutamine, isoleucine, leucine, lysine, ornithine, proline, serine, threonine, tryptophan and valine. The agent is particularly suited for the fermentation production of glutamic acid and lysine. Examples of the carboxylic acid available by the fermentation production include citric acid, acetic acid, propionic acid, lactic acid, fumaric acid, tartaric acid, itaconic acid, α-ketoglutaric acid, ascorbic acid, gluconic acid, malic acid and kojic acid. The agent is particularly suited for the fermentation production of citric acid and ascorbic acid. Examples of the enzyme available by the fermentation production include α-amylase, β-amylase, protease, lipase, cellulase, pectinase and gluco amylase. The agent is particularly suited for the fermentation production of cellulase. Examples of the the antibiotic available by the fermentation production include β-lactam antibiotics such as penicillin, aminoglucoside antibiotics such as kanamycin, chloramphenicol antibiotics, tetracycline antibiotics such as chlorotetracycline, macrolide antibiotics such as erythromycin, peptide antibiotics such as gramicidin S, antibacterial antibiotics such as mikamycin, novobiocin and lincomycin, antitumor antibiotics such as actinomycin D and chromomycin $A_3$, and antifungal antibiotics such as azalomycin. The agent is particularly suited for the fermentation production of glutamic acid and citric acid out of these.

Although there is no particular limitation imposed on the culturing means to which the fermentation production process of the present invention can be applied, the process can be applied suitably to aerated culture, spinner culture, shaking culture or the like by which a large amount of foams is formed.

EXAMPLES

The present invention will hereinafter be described more specifically by the following examples. It is, however, to be borne in mind that the present invention is by no means limited to or by them.

Compounds used as antifoaming agents in the below-described examples are shown in Table 1.

TABLE 1

|  | Oil or fat | Alcohol | Alkylene oxide | Molar ratio*[1] |
|---|---|---|---|---|
| Comparative product | | | | |
| 1 | Tallow | Glycerin | (PO) (EO)block | 1/0.3/80/40 |
| 2 | Hardened palm oil | Pentaerythritol | (PO) (EO) (PO)block | 1/1/30/25/20 |
| 3 | Soybean oil | Sucrose | (PO) (EO)random | 1/0.5/(100/50) |
| 4 | Coconut oil | Glycerin | (PO) (EO)block | 1/0.6/45/20 |
| 5 | Polypropylene glycol (Mw: 3,000) | | | |
| 6 | Tallow alcohol | | | |
| 7 | Oleyl alcohol/EO/PO/EO = 1/5/30/10 | | | |
| 8 | Coconut oil fatty acid | | | |
| 9 | Glycerin/PO/EO/PO = 1/20/20/20 | | | |
| Invention product | | | | |
| 1 | a 30:70 mixture of Comparative Product 1 and Comparative Product 5 | | | |
| 2 | a 50:20:30 mixture of Comparative Product 1, Comparative Product 8 and Comparative Product 9 | | | |
| 3 | a 60:40 mixture of Comparative Product 1 and Comparative Product 6 | | | |
| 4 | a 40:20:40 mixture of Comparative Product 2, Comparative Product 6 and Comparative Product 7 | | | |
| 5 | a 40:40:20 mixture of Comparative Product 2, Comparative Product 5 and Comparative Product 8 | | | |
| 6 | a 50:50 mixture of Comparative Product 2 and Comparative Product 9 | | | |
| 7 | a 40:60 mixture of Comparative Product 3 and Comparative Product 7 | | | |
| 8 | a 50:25:25 mixture of Comparative Product 3, Comparative Product 6 and Comparative Product 8 | | | |
| 9 | a 40:20:40 mixture of Comparative Product 3, Comparative Product 5 and Comparative Product 7 | | | |
| 10 | a 70:15:15 mixture of Comparative Product 4, Comparative Product 5 and Comparative Product 6 | | | |
| 11 | a 80:20 mixture of Comparative Product 4 and Comparative Product 8 | | | |
| 12 | a 40:40:20 mixture of Comparative Product 4, Comparative Product 7 and Comparative Product 9 | | | |

*[1]oil or fat/alcohol/propylene oxide and ethylene oxide

Example 1

In a medium containing 10 wt. % (in terms of sugar) of cane molassess, 0.5 wt. % of urea and 0.3 wt. % of corn steep liquor, *Corynebacterium glutamicum* was inoculated and cultured in a Sakaguchi flask at 31.5° C. At the beginning of the logarithmic growth phase, polyoxyethylene monopalmitate was added to the medium in an amount of 0.15 wt. %, followed by culturing at 33° C. for 10 hours.

In a 500-ml measuring cylinder, a 100-ml portion of the culture solution so obtained was weighed, to which air was fed at 5 l/min. At the point when foams reached 300 ml, a 10 wt. % aqueous solution of the invention product or comparative product was added in an amount of 0.01 g. Subsequent to the aeration for 30 minutes, the height of foams (ml) was measured. The results are shown in Table 2.

TABLE 2

| | | antifoaming effects | |
|---|---|---|---|
| | | Foam-inhibiting property (ml) (foam height) | Foam-breaking property (immediately after the addition) |
| Invention Product | 1 | 250 | Good foam break |
| | 3 | 220 | Good foam break |
| | 4 | 200 | Good foam break |
| Comparative Product | 1 | 400 | Not so good foam break |
| | 2 | 380 | Not so good foam break |
| | 5 | 500 or greater | Poor foam break |
| | 6 | 500 or greater | Poor foam break |
| | 7 | 500 or greater | Poor foam break |

As is apparent from Table 2, any one of the invention products had excellent foam-inhibiting property and foam-breaking property. On the other hand, Comparative Product 5, 6 or 7 was added as an antifoaming agent whenever foams reached 300 ml. Although the addition was conducted even 5 times, no foam-height-inhibiting effects were recognized.

Example 2

| Molassess | 300 g |
|---|---|
| $NH_4Cl$ | 1 g |
| $KH_2PO_4$ | 0.5 g |
| $MgSO_4.7H_2O$ | 0.5 g |
| tap water | balance |
| Total | 1,000 ml |

In a 3-l jar fermenter, 1 l of a medium for the fermentation of citric acid, said medium having the above composition, was charged, followed by sterilization treatment at 121° C. for 15 minutes. On the side, *Aspergillus niger* which had been inoculated as a seed culture in two potato-dextrose-charged petri dishes of 9 cm in diameter was suspended in a 5 cc of sterilized water, followed by inoculating in the above medium. A foam sensor was installed at 5 cm downward from the upper part of the jar so that a 15 wt. % aqueous solution of the invention product or comparative product would automatically be added dropwise at the point when foams were brought into contact with the sensor during culturing. The culturing was conducted for 6 days at 30° C., 600 rpm and 1 vvm. The production amount of citric acid and amount of the antifoaming agent used are shown in Table 3.

TABLE 3

| | | Amount of citric acid produced (g/l) | Amount (g) of antifoaming agent used (in terms of original solution) |
|---|---|---|---|
| Invention Product | 2 | 85 | 2.4 |
| | 5 | 83 | 2.2 |
| | 6 | 86 | 2.4 |
| Comparative Product | 1 | 74 | 6.8 |
| | 2 | 77 | 6.4 |
| | 5 | 62 | 11.5 |
| | 8 | 60 | 10.9 |
| | 9 | 61 | 12.1 |

As is apparent from Table 3, the invention product exhibited antifoaming effects in an amount smaller than that of the comparative product. In addition, it showed excellent effects on an increase in the production yield.

Example 3

| Wheat bran | 50 g |
|---|---|
| Peptone | 10 g |
| $K_2HPO_4$ | 1 g |
| $MgSo_4.7H_2O$ | 0.2 g |
| Yeast extract | 5 g |
| $Na_2CO_3$ | 10 g |
| Water | balance |
| Total | 1,000 ml |

In a medium for enzyme production, said medium having the above-described composition, *Bacillus sp.* was inoculated so that the absorbance at 600 nm would become 1.0, followed by culturing at 33° C. for 36 hours while adding with an antifoaming agent in a similar manner to Example 2. The amount of cellulase produced and the amount of the antifoaming agent used are shown in Table 4.

TABLE 4

| | | Amount of cellulase produced (U/l) | Amount (g) of antifoaming agent used (in terms of original solution) |
|---|---|---|---|
| Invention Product | 7 | 14,500 | 1.9 |
| | 9 | 15,000 | 2.0 |
| | 10 | 14,000 | 2.0 |
| Comparative Product | 3 | 12,500 | 6.6 |
| | 4 | 13,000 | 6.3 |
| | 5 | 12,000 | 8.5 |
| | 6 | 12,500 | 10.1 |
| | 7 | 12,000 | 9.2 |

As is apparent from Table 4, the invention product exhibited antifoaming effects in an amount smaller than that of the comparative product and in addition, it showed excellent effects on an increase in the production yield.

Example 4

| Meat extract | 10 g |
|---|---|
| Peptone | 10 g |
| NaCl | 5 g |
| Water | Balance |
| Total | 1,000 ml |

In a petri dish having a diameter of 9 cm, *Streptmyces sp.* was preliminarily cultured in a agar medium which had been obtained by the addition of 1.5% of agar to the above medium composition, followed by suspending in 10 cc of sterilized water. The suspension so obtained was inoculated in 1 l of the antibiotic medium having the above composition, followed by cultured at 35° C. for 72 hours while adding an antifoaming agent in a similar manner to Example 2. The amount of the antifoaming agent used is shown in Table 5.

TABLE 5

|  |  | Amount (g) of anti-foaming agent used (g) (in terms of original solution) |
|---|---|---|
| Inven- | 8 | 3.1 |
| tion | 11 | 2.8 |
| Product | 12 | 2.9 |
| Compa- | 3 | 6.4 |
| rative | 4 | 5.8 |
| Product | 6 | 8.6 |
|  | 7 | 8.8 |
|  | 8 | 7.9 |
|  | 9 | 9.1 |

As is apparent from Table 5, the invention product exhibited excellent antifoaming effects in an amount smaller than that of the comparative product.

Example 5

| Cane molassess | 200 g |
| Urea | 20 g |
| $K_2HPO_4$ | 4 g |
| Water | balance |
| Total | 1,000 ml |

In a 3-l jar fermenter, 1,200 ml of a medium having the above composition were charged, to which *Brevibacterium flavum* (O.D.=30, 100 ml) which had been preliminarily cultured in the above medium was inoculated, followed by culturing at 32° C. At the beginning of the logarithmic growth phase, polyoxyethylene monopalmitate was added to the cultured medium in an amount of 0.20 wt. %, followed by culturing for 30 hours. During the culturing, pH was adjusted to 7.5 with aqueous ammonia and addition was conducted to give a sugar concentration of 3% as a lower limit. An antifoaming agent was added in accordance with Example 2. The amount of the antifoaming agent and the production amount of L-glutamic acid (L-GA) are shown in Table 6.

TABLE 6

|  |  | Amount of L-GA produced (g/l) | Amount (g) of anti-foaming agent used (in terms of original solution) |
|---|---|---|---|
| Inven- | 1 | 93 | 1.8 |
| tion | 4 | 91 | 2.1 |
| Product |  |  |  |
| Compa- | 1 | 81 | 5.2 |
| rative | 2 | 80 | 6.1 |
| Product | 5 | 65 | 17.5 |

TABLE 6-continued

|  |  | Amount of L-GA produced (g/l) | Amount (g) of anti-foaming agent used (in terms of original solution) |
|---|---|---|---|
|  | 6 | 68 | 25.0 |
|  | 7 | 77 | 22.0 |

As is apparent from Table 6, the invention product exhibited excellent antifoaming effects and L-GA productivity in an amount smaller than that of the comparative product.

CAPABILITY OF EXPLOITATION IN INDUSTRY

The antifoaming agent according to the present invention for fermentation has both foam-breaking effects and foam-inhibiting effects so that it has excellent antifoaming effects, and does not adversely affect the fermentation production.

What is claimed is:

1. An antifoaming agent for fermentation, which comprises the following components (A) and (B):

(A) a reaction product obtained by the addition polymerization of 80 to 200 moles in total of ethylene oxide and propylene oxide (the molar ratio of ethylene oxide to propylene oxide=1:1 to 1:4) to 1 mole of a mixture composed of an oil or fat and a polyhydric alcohol containing at least three hydroxyl groups, said mixture having the molar ration of the oil or fat component to the polyhydric alcohol component=1:0.2–1:1; and (B) at least one compound selected from the group consisting of:
 (1) fatty acids,
 (2) alcohols,
 (3) polyoxyalkylene polyhydric alcohol ethers,
 (4) polyoxyalkylene alkyl ethers,
 (5) polyoxyalkylene fatty acid esters,
 (6) polyoxyalkylene alkyl ether fatty acid esters, and
 (7) polyoxyalkylene polymers.

2. An antifoaming agent according to claim 1, wherein in the component (A), the molar ratio of ethylene oxide to propylene oxide falls within a range of from 1:1.5 to 1:2.5.

3. An antifoaming agent according to claim 1, wherein the component (B) is the polyoxyalkylene polymer (7).

4. An antifoaming agent according to claim 1, wherein the component (B) is a polypropylene glycol or polyoxypropylene-polyoxyethylene copolymer having an average molecular weight of 2,000 to 10,000.

5. An antifoaming agent according to claim 1, which comprises the component (A) and the component (B) in a weight ratio of 5:95 to 95:5.

6. An antifoaming agent according to claim 1, which is suitable for use in amino acid fermentation, carboxylic acid fermentation, enzyme fermentation or antibiotic fermentation.

7. A process for the fermentation production of an amino acid, a carboxylic acid, an enzyme or an antibiotic, which comprises adding an antifoaming agent of claim 1 to a culture medium in an amount of 0.0001 to 2 wt. % and culturing microorganisms therein.

* * * * *

UNITED STATES PATENT AND TRADEMARK OFFICE
CERTIFICATE OF CORRECTION

PATENT NO.  : 5,843,734
DATED       : December 1, 1998
INVENTOR(S) : Shonaka et al.

It is certified that error appears in the above-identified patent and that said Letters Patent is hereby corrected as shown below:

Claim 1, column 10, line 31, change "ration" to --ratio--.

Signed and Sealed this

Nineteenth Day of October, 1999

Attest:

Q. TODD DICKINSON

Attesting Officer

Acting Commissioner of Patents and Trademarks